US006217855B1

(12) United States Patent
Itou et al.

(10) Patent No.: US 6,217,855 B1
(45) Date of Patent: Apr. 17, 2001

(54) HAIR TREATMENT COMPOSITION

(75) Inventors: Takashi Itou; Takayoshi Kajino; Aya Miyaji, all of Chiba; Toru Yoshihara, Tokyo; Jiro Kawase, Chiba; Mikako Matubara; Naohisa Kure, both of Tokyo, all of (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 08/864,973

(22) Filed: May 29, 1997

Related U.S. Application Data

(63) Continuation of application No. 08/698,820, filed on Aug. 16, 1996, now abandoned, which is a continuation of application No. 08/421,135, filed on Apr. 13, 1995, now abandoned, which is a continuation of application No. 08/131,575, filed on Oct. 4, 1993, now abandoned, which is a continuation of application No. 07/928,025, filed on Aug. 11, 1992, now abandoned.

(30) Foreign Application Priority Data

| Aug. 14, 1991 | (JP) | 3-204372 |
|---|---|---|
| Aug. 14, 1991 | (JP) | 3-204373 |
| Aug. 15, 1991 | (JP) | 3-205267 |
| Aug. 15, 1991 | (JP) | 3-205268 |
| Apr. 9, 1992 | (JP) | 4-088841 |
| Apr. 9, 1992 | (JP) | 4-088842 |
| Apr. 10, 1992 | (JP) | 4-090721 |
| Apr. 10, 1992 | (JP) | 4-090722 |

(51) Int. Cl.$^7$ .............. A61K 7/06; A61K 7/09; A61K 7/13

(52) U.S. Cl. .............. 424/70.2; 424/70.1; 8/405; 8/431; 8/433; 132/202; 132/203; 132/204; 132/210

(58) Field of Search .................. 424/70.1, 70.2, 424/70.6; 8/405, 431, 433; 132/202, 203, 204, 210

(56) References Cited

U.S. PATENT DOCUMENTS 4,313,933 * 2/1982 Yamazaki .................. 424/72
4,844,866 * 7/1989 Hartmann .................. 424/70
5,133,972 * 7/1992 Ferrini .................. 514/80
5,164,177 * 11/1992 Bhah .................. 424/47
5,254,333 * 10/1993 Kasino .................. 424/70

FOREIGN PATENT DOCUMENTS

| 0193932 | 9/1986 | (EP) . |
| 0330193 | 8/1989 | (EP) . |
| 2627085 | 8/1989 | (EP) . |
| 2380025 | 9/1978 | (FR) . |
| 2627085 | 8/1989 | (FR) . |
| 880926 | 10/1961 | (GB) . |

OTHER PUBLICATIONS

Wolfram et al, *Journal of the Society of Cosmetic Chemists*, "Torsional Behavior of Human Hair" pp. 87–99 (1985).*

Derwent Abstract of J02218605.

Derwent Abstract of J60087208.

Derwent Abstract of J50088241.

Patent Abstracts of Japan. Abstract of JP–A 3 157 321.

Derwent Abstract of JP–A 2 218 605.

Derwent Abstract of JP–A 60 087 208.

Derwent Abstract of JP–A 50 088 241.

* cited by examiner

*Primary Examiner*—Thurman K. Page
*Assistant Examiner*—Brian K. Seidleck
(74) *Attorney, Agent, or Firm*—Sughrue, Mion, Zinn, Macpeak & Seas, PLLC

(57) ABSTRACT

The present invention provides a hair treatment composition (I) comprising the following components (a) and (b), or a hair treatment composition (II) comprising the following components (c) and (b), and a method for imparting elasticity to the hair using the composition:

(a) an organic solvent;
(b) at least one aromatic sulfonic acid selected from naphthalenesulfonic acids, azulenesulfonic acids, tetralin-sulfonic acids, indansulfonic acids and benzophenonesulfonic acids or salts thereof; and
(c) a reducing agent.

31 Claims, No Drawings

HAIR TREATMENT COMPOSITION

This is a Continuation of application Ser. No. 08/698,820 filed Aug. 16, 1996, now abandoned, which is a continuation of application Ser. No. 08/421,135 filed Apr. 13, 1995, now abandoned, which is a continuation of application Ser. No. 08/131,575 filed Oct. 4, 1993, now abandoned, which is a continuation of application Ser. No. 07/928,025 filed Aug. 11, 1992 now abandoned.

FIELD OF THE INVENTION

This invention relates to a hair treatment composition capable of imparting high elasticity to the hair.

BACKGROUND OF THE INVENTION

Troubles due to low elasticity of the hair (for example, low tension, poor firmness and less bulkiness) amount to a considerable part in problems on the hair. In order to satisfy the requirements by those having these troubles, there have been marketed a number of hair treatment compositions containing elasticity imparting components and conditioning components. However, these components are adsorbed on the surface of the hair to thereby exert the desired effects. Since these components are washed away upon shampooing, it is needed to apply them repeatedly, which requires troublesome procedures. On the other hand, attempts have been made to penetrate active components into the hair so as to achieve the desired effects. For example, there has been reported a method for treating the hair with an aqueous solution of naphthalenesulfonic acid [refer to *J. Soc. Cosmet. Chem.*, 36, 87–99 (1985)]. However, since the naphthalenesulfonic acid cannot sufficiently penetrate into the hair, a long time is required for the completion of the treatment, and this method cannot give any satisfactory effect.

SUMMARY OF THE INVENTION

Under these circumstances, the present inventors have conducted extensive studies. As a result, it has successfully found that the elasticity of the hair can be improved by treating the hair with a composition comprising at least one of an organic solvent and a reducing agent as well as an aromatic sulfonic acid, thus completing the present invention. While said treatment requires only a short period of time, the improved elasticity can be sustained for a long time.

Accordingly, the present invention provides a hair treatment composition (I) comprising the following components (a) and (b), or a hair treatment composition (II) comprising the following components (c) and (b):

(a) an organic solvent;

(b) at least one aromatic sulfonic acid selected from naphthalenesulfonic acids, azulenesulfonic acids, tetralinsulfonic acids, indansulfonic acids and benzophenonesulfonic acids, or salts thereof; and (c) a reducing agent.

DETAILED DESCRIPTION OF THE INVENTION

Hair Treatment Composition (I):

There is no particular limitation in the selection of the organic solvent (a) to be contained in the composition (I) of the present invention, but preferable examples thereof include compounds represented by Formula (1):

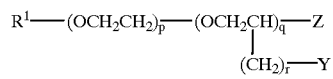

wherein $R^1$ represents a hydrogen atom, an group having 1 to 4 carbon atoms or a group of the formula

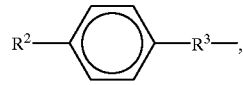

wherein $R^2$ represents a hydrogen atom, a methyl group or a methoxy group and $R^3$ represents a bond or a saturated or unsaturated divalent hydrocarbon group having from 1 to 3 carbon atoms; Y and Z each represents a hydrogen atom or a hydroxyl group; and p, q and r each represents an integer of from 0 to 5, except that all the p, q and r are 0 and Z is a hydrogen atom and that all the p, q and r are 0, $R^1$ is a hydrogen atom and Z is a hydroxyl group; an N-alkyl-pyrrolidone represented by Formula (2):

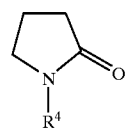

wherein $R^4$ represents a straight-chain or branched alkyl group having from 1 to 18 carbon atoms; and an alkylene carbonates having from 1 to 4 carbon atoms.

Particular examples of the above compounds of Formulae (1)/(2) and the alkylene carbonates as the organic solvents (a) include ethanol, isopropanol, n-propanol, n-butanol, isobutanol, ethylene glycol, propylene glycol, 1,3-butanediol, benzyl alcohol, cinnamyl alcohol, phenethyl alcohol, p-anisyl alcohol, p-methylbenzyl alcohol, phenoxyethanol, 2-benzyloxyethanol, methyl carbitol, ethyl carbitol, propyl carbitol, butyl carbitol, triethylene glycol monoethyl ether, triethylene glycol monobutyl ether, glycerol, N-methylpyrrolidone, N-octylpyrrolidone and N-laurylpyrrolidone, preferably 1,3-butanediol, benzyl alcohol, 2-benzyloxyethanol and N-methylpyrrolidone.

The content of the organic solvent (a) in the composition (I) according to the present invention may range from 0.5 to 50%, preferably from 2 to 30%, by weight based on the total composition. When the content thereof is less than 0.5%, any sufficient effect cannot be achieved. When its content exceeds 50%, on the other hand, the effects cannot be improved any more.

As the aromatic sulfonic acids of the component (b), the following compounds can be illustrated. There is no limitation as to which position the sulfo group presents at in the molecule.

Examples of the naphthalenesulfonic acids to be used as the component (b) in the present invention include those represented by Formula (3) or salts thereof:

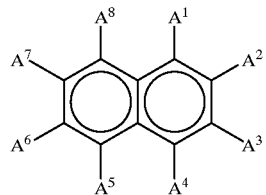

(3)

wherein at least one of $A^1$ to $A^8$ represents a sulfo group or a salt thereof while others each represents a hydrogen atom, a halogen atom, a hydroxyl group, a nitro group, a carboxyl group, a lower alkoxycarbonyl group, an alkyl group, an alkenyl group, a lower alkoxy group, a formyl group, an acyl group, a phenylazo group which may be substitured by the group of —OH, —COOH, —OCH$_3$, —CH$_3$, —CH$_2$CH$_3$ or —NO$_2$ or an —N(R')(R") group, wherein R' and R" each represents a hydrogen atom, a lower alkyl group, a lower alkenyl group, a phenyl group, a benzyl group or an acyl group.

Particular examples of the compounds represented by Formula (3) include 1- or 2-naphthalenesulfonic acid, 2,7-naphthalenedisulfonic acid, 1,5-naphthalenedisulfonic acid, 2,6-naphthalenedisulfonic acid, 1,3,6-naphthalenetrisulfonic acid, 1-naphthol-2-sulfonic acid, 1-naphthol-4-sulfonic acid, 2-naphthol-6-sulfonic acid, 2-naphthol-7-sulfonic acid, 1-naphthol-3,6-disulfonic acid, 2-naphthol-3,6-disulfonic acid, 2-naphthol-6,8-disulfonic acid, 2,3-dihydroxynaphthalene-6-sulfonic acid, 1,7-dihydroxynaphthalene-3-sulfonic acid, chromotropic acid (4,5-dihydroxynaphthalene-2,7-disulfonic acid), 3,6-dihydroxynaphthalene-2,7-disulfonic acid, S acid (1-amino-8-naphthol-4-sulfonic acid), γ acid (2-amino-8-naphthol-6-sulfonic acid), J acid (2-amino-5-naphthol-7-sulfonic acid), H acid (1-amino-8-naphthol-3,6-disulfonic acid), 7-amino-1,3-naphthalenedisulfonic acid, 1-amino-2-naphthol-4-sulfonic acid, 1-naphthylamine-4-sulfonic acid, Bronner's acid (2-naphthylamine-6-sulfonic acid), Krebs acid (1-naphthylamine-7-sulfonic acid), 2-naphthylamine-1-sulfonic acid, 1-naphthylamine-6-sulfonic acid, 1-naphthylamine-8-sulfonic acid, 4-amino-5-hydroxy-8-phenylazo-2,7-naphthalenedisulfonic acid, 4-amino-8-(4-carboxyphenylazo)-5-hydroxy-2,7-naphthalenedisulfonic acid, 6-amino-4-hydroxy-3-phenylazo-2-naphthalenesulfonic acid, 4-amino-8-(4-carboxyphenylazo)-5-hydroxy-1-naphthalenesulfonic acid, 7-amino-4-hydroxy-1-phenylazo-2-naphthalenesulfonic acid, 8-amino-5-(4-carboxyphenylazo)-2-naphthalenesulfonic acid, 4-amino-3-(4-carboxyphenylazo)-5-hydroxy-1-naphthalenesulfonic acid, 6-amino-4-hydroxy-5-phenylazo-2-naphthalenesulfonic acid, 2,7-diamino-1-naphthol-3-sulfonic acid, 7,8-diamino-1-naphthol-3-sulfonic acid, naphthalenesulfonic acid formalin polycondensate (weight-average degree of condensation: 2-100), 6-methyl-2-naphthalenesulfonic acid, 4-ethyl-1-naphthalenesulfonic acid, 5-isopropyl-1-naphthalenesulfonic acid, 5-butyl-2-naphthalenesulfonic acid and salts thereof. Among these compounds, 2-naphthalenesulfonic acid, 1,5-naphthalenedisulfonic acid, 2,6-naphthalenedisulfonic acid, chromotropic acid, 1-naphthalenesulfonic acid, H acid (1-amino-8-naphthol-3,6-disulfonic acid), 2,7-naphthalenedisulfonic acid, naphthalenesulfonic acid polycondensate (weight-average degree of condensation: 2-50) and salts thereof are particularly preferable.

Examples of the azulenesulfonic acids to be used as the component (b) in the present invention include guaiazulenesulfonic acid, 1-azulenesulfonic acid, 3-acetyl-7-isopropyl-1-azulenesulfonic acid, 3-(2-hydroxyethyl)-7-isopropyl-1-azulenesulfonic acid, 3-methyl-7-isopropyl-1-azulenesulfonic acid, 7-isopropyl-1-azulenesulfonic acid, 3-phenyl-6-isopropyl-1-azulenesulfonic acid, 1,4-dimethyl-7-isopropyl-2-azulenesulfonic acid, 4-ethoxy-3-ethyl-6-isopropyl-1-azulenesulfonic acid, 1,3-azulenedisulfonic acid, 4,6,8-trimethyl-1,3-azulenedisulfonic acid, 1,3-bis(1,1-dimethylethyl)-5,7-azulenedisulfonic acid, 1,3-bis(1,1-dimethylethyl)-5-azulenesulfonic acid, 3-formyl-4,6,8-trimethyl-1-azulenesulfonic acid and salts thereof, preferably guaiazulenesulfonic acid.

Examples of the tetralinsulfonic acids and indansulfonic acids to be used as the component (b) in the present invention include compounds represented by Formula (4) or salts thereof:

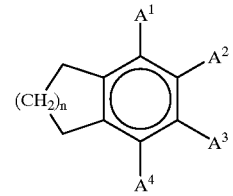

(4)

wherein at least one of $A^1$ to $A^4$ represents a sulfo group or a salt thereof while others each represents a hydrogen atom, a halogen atom, a hydroxyl group, a nitro group, a carboxyl group, a lower alkoxycarbonyl group, an alkyl group, an alkenyl group, a lower alkoxy group, a formyl group, an acyl group or an —N(R')(R") group, wherein R' and R" each represents a hydrogen atom, a lower alkyl group, a lower alkenyl group, a phenyl group, a benzyl group or an acyl group; and n is an integer of 1 or 2.

Among the compounds represented by Formula (4), examples of the tetralinsulfonic acids include 1-tetralinsulfonic acid, 2-tetralinsulfonic acid, 1,3-tetralindisulfonic acid, 5,6,7,8-tetrahydro-1-naphthalenesulfonic acid, 5,6,7,8-tetrahydro-2-naphthalenesulfonic acid, 1,2,3,4-tetrahydro-5,7-naphthalenedisulfonic acid, 1,2,3,4-tetrahydro-6-sulfo-1-naphthol, 1,2,3,4-tetrahydro-6-sulfo-2-naphthoic acid, 1,2,3,4-tetrahydro-6-sulfo-2-naphthol, 1,2,3,4-tetrahydro-7-sulfo-2-naphthoic acid, 1,2,3,4-tetrahydro-5-sulfo-2-naphthoic acid, 1,2,3,4-tetrahydro-8-sulfo-2-naphthoic acid, 1,2,3,4-tetrahydro-5-sulfo-2-naphthol, 1,2,3,4-tetrahydro-7-sulfo-2-naphthol, 1,2,3,4-tetrahydro-8-sulfo-2-naphthol, 5,6,7,8-tetrahydro-3-sulfo-1-naphthol, 5,6,7,8-tetrahydro-3-sulfo-1-naphthylamine, 1,2,3,4-tetrahydro-5-sulfo-1-naphthylamine, 1,2,3,4-tetrahydro-6-sulfo-1-naphthylamine, 1,2,3,4-tetrahydro-7-sulfo-1-naphthylamine, 1,2,3,4-tetrahydro-8-sulfo-1-naphthylamine, 5,6,7,8-tetrahydro-4-methyl-2-naphthalenesulfonic acid, 5,6,7,8-tetrahydro-4-butyl-2-naphthalenesulfonic acid, 5,6,7,8-tetrahydro-4-ethyl-2-naphthalenesulfonic acid, 5,6,7,8-tetrahydro-4-isopropyl-2-naphthalenesulfonic acid, 5,6,7,8-tetrahydro-4-methyl-1-naphthalenesulfonic acid, 5,6,7,8-tetrahydro-4-methoxy-2-naphthalenesulfonic acid and 5,6,7,8-tetrahydro-4-acetyl-2-naphthalenesulfonic acid, preferably 5,6,7,8-tetrahydro-1-naphthalenesulfonic acid and 5,6,7,8-tetrahydro-2-naphthalenesulfonic acid. On the other hand, examples of the indansulfonic acids, from among those represented by Formula (4), include 1-indansulfonic acid, 2-indansulfonic acid, 4-indansulfonic acid, 5-indansulfonic acid, 4,6-indandisulfonic acid, 4-sulfo-1-indanol, 5-sulfo-1-indanol, 6-sulfo-1-indanol, 7-sulfo-1-indanol, 4-sulfo-2-indanol, 5-sulfo-2-indanol, 2-bromo-5-sulfo-1-indanol, 7-sulfo-5-indanol, 6-sulfo-5-indanol, 1-carboxy-5-indansulfonic acid, 7-methoxy-5-indansulfonic acid, 7-acetyl-5-indansulfonic acid, 7-methyl-5-indansulfonic acid, 7-methyl-4-indansulfonic acid, 7-butyl-5-indansulfonic acid, 7-ethyl-5-indan sulfonic acid and 7-isopropyl-5-indansulfonic acid, preferably 4-indansulfonic acid and 5-indansulfonic acid.

Examples of the benzophenonesulfonic acids to be used as the component (b) in the present invention include those represented by Formula (5) or salts thereof:

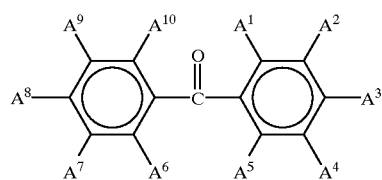

(5)

wherein at least one of $A^1$ to $A^{10}$ represents a sulfo group or a salt thereof while others each represents a hydrogen atom, a halogen atom, a hydroxyl group, a nitro group, a carboxyl group, a lower alkoxycarbonyl group, an alkyl group, an alkenyl group, a lower alkoxy group, a formyl group, an acyl group or an —N(R')(R") group, wherein R' and R" each represents a hydrogen atom, a lower alkyl group, a lower alkenyl group, a phenyl group, a benzyl group or an acyl group.

Particular examples of the compounds represented by Formula (5) include 2-hydroxy-4-methoxybenzophenone-5-sulfonic acid, 2,2'-dihydroxy-4,4'-dimethoxy-5,5'-benzophenonedisulfonic acid, o-chlorobenzophenonesulfonic acid, p-chlorobenzophenonesulfonic acid, 4,4'-dichlorobenzophenonesulfonic acid, 2,4"-dichlorobenzophenonesulfonic acid, 2,4-dichlorobenzophenonesulfonic acid, 2-hydroxybenzophenonesulfonic acid, 4-hydroxybenzophenonesulfonic acid, 2-aminobenzophenonesulfonic acid, 4-aminobenzophenonesulfonic acid, 2-methylbenzophenonesulfonic acid, 4-methoxybenzophenonesulfonic acid, 4,4'-dimethylbenzophenonesulfonic acid, 4,4'-dimethoxybenzophenonesulfonic acid and 4-chloro-4'-hydroxybenzophenonesulfonic acid. Among these compounds, 2-hydroxy-4-methoxybenzophenone-5-sulfonic acid and 2,2'-dihydroxy-4,4'-dimethoxy-5,5'-benzophenonedisulfonic acid are particularly preferable.

In the above formulae (3) to (5), examples of halogen atoms include a fluorine atom, a chlorine atom and a bromine atom; examples of acyl groups include acetyl group; carbon number of an alkyl group and an alkenyl group may be from 1 to 18; and the term "lower" means the carbon number being from 1 to 4.

As the above-mentioned salts of the aromatic sulfonic acids, sodium salts, potassium salts, lithium salts, calcium salts, ammonium salts and organic quaternary ammonium salts may be illustrated.

Either one of these aromatic sulfonic acids or a mixture thereof may be used as the component (b) in the present invention. The content of the aromatic sulfonic acids (b) in the composition (I) may range from 0.1 to 10%, preferably from 1 to 5%, by weight based on the total composition. When the content of these aromatic sulfonic acids is less than 0.1%, the desired hair-treatment effects cannot be fully achieved. When this content exceeds 10%, on the other hand, the effects cannot be improved any more.

It is preferred that the hair treatment composition (I) according to the present invention further contains an acid or an alkali so as to adjust its pH value within a specific range, since the hair thus sufficiently swells and, as a result, the penetration of the aromatic sulfonic acids (b) or indansulfonic acids into the hair can be promoted. That is to say, it is preferable to adjust the pH value of the composition (I) to 2 to 5 by adding an acid or to 8 to 11 by adding an alkali. When the pH value of the composition (I) is less than 2 or exceeds 11, there is a risk that the hair is damaged. Bhat et al. reported swelling of the hair due to acids or alkalis [G. Ramachandra Bhat et al., *J. Soc. Cosmet. Chem.*, 32f, 393–405 (1981)], in which report, hydrochloric acid and sodium hydroxide were employed respectively as an acid and an alkali. In the present invention, however, it is preferable to use an organic acid or phosphoric acid as an acid and ammonia or an organic amine as an alkali, since the hair has an ion-exchanging action.

Examples of the above-mentioned organic acid include citric acid, glycolic acid, succinic acid, tartaric acid, lactic acid, acetic acid, fumaric acid, malic acid, levulinic acid, butyric acid, valeric acid, oxalic acid, maleic acid, phthalic acid and mandelic acid. Examples of the above-mentioned organic amines include monoethanolamine, diethanolamine, triethanolamine, aminohydroxymethyl propanediol, 2-amino-2-methyl-1-propanol, 2-amino-2-methyl-1,3-propanediol and basic amino acids such as arginine.

Either one of these acids and alkalis or a combination thereof may be used. These components may be added in such an amount as to adjust the pH value of the composition (I) within the range as specified above. The content thereof preferably range from 0.3 to 50%, still preferably from 0.5 to 30%, by weight based on the total composition. When the content thereof is less than 0.3%, the hair cannot swell because of the ion-exchanging action of the hair per se. When it exceeds 50%, on the other hand, the effects cannot be improved any more.

Usually, the hair treatment composition (I) according to the present invention contains the above-mentioned organic solvent (a), aromatic sulfonic acids (b), acid or alkali together with the balance of water. Although depending on the solubility of the organic solvent (a), the ratio of the organic solvent (a) to water preferably ranges from 20/80 to 50/50.

It is preferable, alternately, that the hair treatment composition (I) of the present invention further contains, for example, a sodium, potassium or ammonium salt of an organic acid such as citric acid, lactic acid, succinic acid, glycolic acid and acetic acid or phosphoric acid, in an amount of from 0.1 to 10% by weight based on the total composition, so as to form a buffer system of pH 2 to 11.

On the use, the hair treatment composition (I) of the present invention may be applied to the hair and allowed to stand for a definite period of time (preferably 5 to 30 minutes), followed by washing away. During the standing period, the hair may be heated to an appropriate temperature (preferably 30 to 50° C.). The hair treatment composition (I) of the present invention may be applied either to dry hair or to moist hair after shampooing.

Hair Treatment Composition (II):

In the hair treatment composition (II) according to the present invention, a reducing agent (c) would cleave cystine in the hair so as to make the hair to swell, thus promoting the rapid penetration of the aromatic sulfonic acid (b) into the hair. Therefore, the composition (II) can be used in a two-agent system wherein the application of the first agent containing the reducing agent (c) is followed by the second agent containing the aromatic sulfonic acids (b).

Examples of the reducing agent (c) include thioglycolic acid and salts thereof (preferably ammonium salt, alkali metal salts such as sodium salt and potassium salt and alkaline earth metal salts such as calcium salt), cysteine and salts thereof (preferably hydrochloride), N-acetyl-L-cysteine and salts thereof (preferably hydrochloride), glycerylmonothioglycolate, thioglyceryl ether (as disclosed in JP-A-2-154919), sulfites and hydrogensulfites (preferably ammonium salt, alkali metal salt such as sodium salt and potassium salt and alkaline earth metal salt such as calcium salt).

Among these reducing agents, thioglycolic acid, ammonium thioglycolate, N-acetyl-L-cysteine, sodium hydrogensulfite and ethoxyethoxyhydroxy propanethiol are particularly preferable.

The content of the reducing agent (c) in the composition (II) of the present invention may range from 0.1 to 10%, preferably from 1 to 7%, by weight based on the total composition or, in the case of the two-agent system, on the first agent. When the content of the reducing agent is less than 0.1%, any sufficient effect cannot be achieved. When it exceeds 10%, on the other hand, the effects cannot be improved any more but the hair is seriously damaged.

In addition, the hair treatment composition (II) of the present invention may further contain alkaline substances such as aqueous ammonia, ethanolamine, ammonium carbonate, ammonium hydrogencarbonate and usea in an amount of 0.1 to 10% by weight based on the total composition, so as to promote the reducing action of the reducing agent (c).

The aromatic sulfonic acids (b) as described above may be contained in the composition (II) of the present invention in the aforementioned content. In the case of the two-agent sysyem, the aromatic sulfonic acids (b) may be contained in the second agent in the same content.

If desired, the organic solvent (a) as described above may be further added in the composition (II) of the present invention in the aforementioned content, so as to enhance the solubility of the aromatic sulfonic acids (b), thus promoting the penetration thereof into the hair. In the case of the two-agent sysyem, the organic solvent (a) may be contained in the second agent in the same content.

On the use, the hair treatment composition (II) of the present invention may be uniformly applied to the hair and then allowed to stand for a definite period of time (preferably from 5 to 30 minutes), followed by washing away. The composition (II) may be applied either to dry hair or moist hair after shampooing. During the standing period, the hair may be heated to an appropriate temperature (preferably from 30 to 50° C.).

The above application of the composition (II) can be separated into two applications of the first agent and the second agent as two-agent system. In this case, the application of the second agent may be conducted either without or after washing away the first agent.

It is preferred that the hair thus treated with the composition (II) is further treated with a composition containing an oxidant such as a peroxide (for example, hydrogen peroxide, sodium percarbonate, sodium perborate), bromic acid or a bromate (for example, potassium bromate, sodium bromate) to thereby rebind cystine bonds cleaved with the reducing agent (c).

The hair treatment composition of the present invention may further contain other components such as thickeners (for example, hydroxyethylcellulose), surfactants, perfumes, pearling agents, colorants, UV absorbers, antioxidants and preservatives, if desired, so long as the effects of the present invention are not deteriorated thereby. In addition, it may contain cationic polymers such as cationized cellulose or silicone derivatives such as dimethyl polysiloxane or amino-denatured silicone so as to improve the texture of the hair or the skin.

The hair treatment composition according to the present invention makes it possible to impart sufficient elasticity to the hair, even by the treatment for short period of time, and the effects thus achieved can be sustained for a prolonged period of time.

The following examples of the present invention are given by way of illustration and not by way of limitation. Unless otherwise indicated, all parts, percents, ratios, etc. used in the examples are by weight.

EXAMPLES 1 TO 16 AND COMPARATIVE EXAMPLES 1 TO 7

Hair treatment compositions were prepared according to Table 1 and evaluated on the elasticity-imparting effect thereof as follows.

The hair of a Japanese female which had not been subjected to cosmetic treatments of cold perm and bleach were banded to 10 g of bundle. Half of thus prepared hair bundle was treated with the composition to be evaluated at 40° C. for 30 minutes. After washing away the composition, the hair bundle was dried using a dryer to perform a pair comparison evaluation on "tension and firmness" of the hair. The evaluation was based on the sense of touch by 5 professional panelists using the following evaluation criteria.

4 points: much more feeling tensile/firm 3 points: more feeling tensile/firm 2 points: feeling tensile/firm at the same level 1 point: less feeling tensile/firm The hair treatment composition which obtained the sum of 18 points or higher in the above criteria would be evaluated as "A". Similarly, the samples obtaining 13 to 17 points, 8 to 12 points and 7 points or lower would be evaluated as "B", "C" and "D", respectively.

Furthermore, the same evaluation was performed in terms of a hair bundle which had been further subjected to shampooing and drying 4 times.

The results obtained are shown in Table 1.

EXAMPLES 17 TO 25 AND COMPARATIVE EXAMPLE 8

Hair treatment compositions were prepared according to Table 2 and evaluated on the elasticity-imparting effect thereof in the same manner as in Examples 1 to 16 except that an oxidation treatment with an aqueous solution of 8% sodium bromate followed the treatment with the composition.

The results obtained are shown in Table 2.

EXAMPLES 26 TO 34 AND COMPARATIVE EXAMPLE 9

The same hair bundle as in Examples 1 to 16 was treated with a first agent (6.0% ammonium thioglycolate, 3.0% ammonium hydrogencarbonate and ammonia water in such an amount that the pH of the agent was 8.5) at 30° C. for 10 minutes. After washing with water, the hair bundle was further treated with a second agent containing the components as shown in Table 3 at 40° C. for 30 minutes followed by an oxidation treatment with an aqueous solution of 8% sodium bromate. After washing with water, the hair bundle was dried using a dryer to perform a pair comparison evaluation on "tension and firmness" of the hair.

The results obtained are shown in Table 3.

EXAMPLES 35 TO 37

The hair/treatment compositions containing the following components were each prepared and evaluated on the elasticity-imparting effect thereof in the same manner as in Examples 1 to 16.

EXAMPLE 35

| | |
|---|---|
| 2-benzyloxyethanol | 10.0% |
| ethanol | 20.0 |
| sodium citrate | 0.1 |
| citric acid | 0.5 |
| lactic acid | 5.0 |
| sodium 2-naphthalenesulfonate | 3.0 |
| stearyltrimethylammonium chloride | 1.0 |
| cetanol | 0.2 |
| propyleneglycol | 3.0 |
| hydroxyethylcellulose | 0.8 |
| perfume | 0.1 |
| water | balance |
| | (pH = 2.8) |

EXAMPLE 36

| | |
|---|---|
| N-methylpyrrolidone | 10.0% |
| ethanol | 15.0 |
| sodium lactate | 1.2 |
| lactic acid | 6.0 |
| sodium 2-tetralinsulfonate | 3.0 |
| cetyltrimethyl ammonium chloride | 1.0 |
| cetanol | 0.2 |
| propyleneglycol | 3.0 |
| perfume | 0.1 |
| water | balance |
| | (pH = 2.8) |

EXAMPLE 37

| | |
|---|---|
| benzylalcohol | 5.0% |
| ethanol | 20.0 |
| monoethanolamine | 3.0 |
| ammonium chloride | 3.0 |
| sodium 2-hydroxy-4-methoxy-benzophenone-5-sulfonate | 3.0 |
| stearyltrimethylammonium chloride | 1.0 |
| cetanol | 0.2 |
| propyleneglycol | 3.0 |
| perfume | 0.1 |
| water | balance |
| | (pH = 9.2) |

As a result, the hair treated with each of the hair treatment compositions showed a sufficient tension and firmness as compared with untreated hair, which properties were confirmed even after 4 shampooings.

EXAMPLE 38

The hair treatment compositions containing the following components were prepared and evaluated on the elasticity-imparting effect thereof in the same manner as in Examples 17 to 25.

| | |
|---|---|
| N-acetyl-L-cysteine | 1.5% |
| sodium 2-naphthalenesulfonate | 3.0 |
| stearyltrimethylammonium chlorate | 1.0 |
| cetanol | 0.2 |
| propyleneglycol | 3.0 |
| hydroxyethylcellulose | 1.0 |
| perfume | 0.1 |
| sodium hydroxide | proper |
| water | balance |
| | (pH = 7) |

As a result, the hair treated with the hair treatment composition showed a sufficient tension and firmness as compared with untreated hair, which properties were confirmed even after 4 shampooings.

EXAMPLE 39

The hair treatment compositions containing the following components were prepared and evaluated on the elasticity-imparting effect thereof in the same manner as in Example 38.

| | |
|---|---|
| sodium hydrogensulfite | 4.0% |
| sodium 2-hydroxy-4-methoxy-benzophenone-5-sulfonate | 1.0 |
| stearyltrimethylammonium chlorate | 1.0 |
| cetanol | 0.2 |
| propyleneglycol | 3.0 |
| hydroxyethylcellulose | 0.5 |
| perfume | 0.1 |
| coloring agent | a little |
| water | balance |
| | (pH = 6) |

As a result, the hair treated with the hair treatment composition showed a sufficient tension and firmness as compared with untreated hair, which properties were confirmed even after 4 shampooings.

TABLE 1

| | Examples | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| benzyl alcohol | 5.0 | — | — | 5.0 | — | 5.0 | 5.0 | 5.0 | 5.0 | 5.0 | — | 5.0 | — | 5.0 | 5.0 | 5.0 |
| 2-benzyl-oxyethanol | — | 5.0 | 5.0 | — | 5.0 | — | — | — | — | — | 5.0 | — | 5.0 | — | — | — |
| ethanol | 20.0 | 20.0 | — | 20.0 | 20.0 | 20.0 | 20.0 | — | 20.0 | 20.0 | 20.0 | 20.0 | 20.0 | 20.0 | — | 20.0 |
| propyleneglycol | — | — | 20.0 | — | — | — | — | 20.0 | — | — | — | — | — | — | 20.0 | — |
| sodium lactate | 1.2 | 1.2 | 1.2 | 1.2 | — | — | 1.2 | 1.2 | — | — | — | — | 1.2 | 1.2 | — | — |
| lactic acid | 6.0 | 6.0 | 6.0 | 6.0 | — | — | 6.0 | 6.0 | — | — | — | — | 6.0 | 6.0 | — | — |
| monoethanolamine | — | — | — | — | — | — | — | — | 3.0 | 3.0 | — | — | — | — | 3.0 | 3.0 |
| ammonium chloride | — | — | — | — | — | — | — | — | 3.0 | 3.0 | — | — | — | — | 3.0 | 3.0 |
| sodium 2-naphthalene sulfonate | 3.0 | — | — | — | — | — | — | — | — | — | — | — | — | — | — | — |
| sodium chromotropate | — | 3.0 | — | — | — | — | — | — | — | — | — | — | — | — | — | — |
| polycondensation product of sodium 2-naphthalenesulfonate and formalin* | — | — | 3.0 | — | — | — | — | — | — | — | — | — | — | — | — | — |
| sodium guaiazulenesulfonate | — | — | — | 3.0 | — | — | — | — | — | — | — | — | — | — | — | — |
| sodium 5,6,7,8-tetrahydro-2-naphthalenesulfonate | — | — | — | — | 3.0 | — | 3.0 | — | 3.0 | — | — | — | — | — | — | — |
| sodium 5-indansulfonate | — | — | — | — | — | 3.0 | — | 3.0 | — | 3.0 | — | — | — | — | — | — |
| sodium hydroxy-methoxybenzophenonesulfonate | — | — | — | — | — | — | — | — | — | — | 3.0 | — | 3.0 | — | 3.0 | — |
| disodium dihydroxy-dimethoxy-benzophenone-disulfonate | — | — | — | — | — | — | — | — | — | — | — | 3.0 | — | 3.0 | — | 3.0 |
| water | balance | balance | balance | balance | balance | balance | balance | balance | balance | balance | balance | balance | balance | balance | balance | balance |
| pH | 2.8 | 2.8 | 2.8 | 2.8 | 6.0 | 6.0 | 2.8 | 2.8 | 9.2 | 9.2 | 6.0 | 6.0 | 2.8 | 2.8 | 9.2 | 9.2 |
| tension/firmness immediately after treatment | A | A | A | A | B | B | A | A | A | A | B | B | A | A | A | A |
| tension/firmness after 4 shampoos | A | A | A | A | B | B | A | A | B | B | B | B | A | A | B | B |

| | Comparative Examples | | | | | | |
|---|---|---|---|---|---|---|---|
| | 1 | 2 | 3 | 4 | 5 | 6 | 7 |
| benzyl alcohol | 5.0 | 5.0 | — | — | — | — | — |
| 2-benzyl-oxyethanol | — | — | — | — | — | — | — |
| ethanol | 20.0 | 20.0 | — | — | — | — | — |
| propyleneglycol | — | — | — | — | — | — | — |
| sodium lactate | 1.2 | — | — | — | — | — | — |
| lactic acid | 6.0 | — | — | — | — | — | — |
| monoethanolamine | — | 3.0 | — | — | — | — | — |
| ammonium chloride | — | 3.0 | — | — | — | — | — |
| sodium 2-naphthalene sulfonate | — | — | 3.0 | — | — | — | — |

TABLE 1-continued

| | | | | | | | |
|---|---|---|---|---|---|---|---|
| sodium chromotropate | — | — | — | — | — | — | — |
| polycondensation product of sodium 2-naphthalenesulfonate and formalin* | — | — | — | — | — | — | — |
| sodium guaiazulenesulfonate | — | — | — | 3.0 | — | — | — |
| sodium 5,6,7,8-tetrahydro-2-naphthalenesulfonate | — | — | — | — | 3.0 | — | — |
| sodium 5-indansulfonate | — | — | — | — | — | 3.0 | — |
| sodium hydroxymethoxybenzophenonesulfonate | — | — | — | — | — | — | 3.0 |
| disodium dihydroxydimethoxybenzophenonedisulfonate | — | — | — | — | — | — | — |
| water | balance | balance | balance | balance | balance | balance | balance |
| pH | 2.8 | 9.2 | 6.0 | 6.0 | 6.0 | 6.0 | 2.0 |
| tension/firmness immediately after treatment | D | D | B | B | C | C | C |
| tension/firmness after 4 shampoos | C | C | C | C | C | C | C |

(% by weight)

*weight-average degree of polycondensation: 8.2

TABLE 2

| | Examples | | | | | | | | | Comp. Ex. |
|---|---|---|---|---|---|---|---|---|---|---|
| | 17 | 18 | 19 | 20 | 21 | 22 | 23 | 24 | 25 | 8 |
| ammonium thioglycolate | 6.0 | 6.0 | 6.0 | 6.0 | 6.0 | 6.0 | 6.0 | 6.0 | 6.0 | 6.0 |
| ammonium hydrogen carbonate | 3.0 | 3.0 | 3.0 | 3.0 | 3.0 | 3.0 | 3.0 | 3.0 | 3.0 | 3.0 |
| sodium 2-naphthalenesulfonate | 3.0 | — | — | — | — | — | — | — | — | — |
| disodium 2,7-naphthalenedisulfonate | — | 3.0 | — | — | — | — | — | — | — | — |
| disodium 1-amino-8-naphthol-3,6-disulfonate | — | — | 3.0 | — | — | — | — | — | — | — |
| polycondensation product of sodium 2-naphthalenesulfonate and formalin* | — | — | — | 3.0 | — | — | — | — | — | — |
| sodium guaiazulene sulfonate | — | — | — | — | 3.0 | — | — | — | — | — |
| sodium 5,6,7,8-tetrahydro-2-naphthalenesulfonate | — | — | — | — | — | 3.0 | — | — | — | — |
| sodium 5-indansulfonate | — | — | — | — | — | — | 3.0 | — | — | — |
| sodium hydroxymethoxybenzophenonesulfonate | — | — | — | — | — | — | — | 3.0 | — | — |
| disodium dihydroxydimethoxybenzophenonedisulfonate | — | — | — | — | — | — | — | — | 3.0 | — |
| ammonia water | proper | proper | proper | proper | proper | proper | proper | proper | proper | proper |
| water | balance | balance | balance | balance | balance | balance | balance | balance | balance | balance |
| tension/firmness immediately after treatment | A | A | A | A | A | A | A | A | A | C |

TABLE 2-continued

| | Examples | | | | | | | | | Comp. Ex. |
|---|---|---|---|---|---|---|---|---|---|---|
| | 17 | 18 | 19 | 20 | 21 | 22 | 23 | 24 | 25 | 8 |
| tension/firmness after 4 shampoos | A | A | A | A | A | A | A | A | A | C |

(% by weight)

*weight-average degree of polycondensation: 8.2

TABLE 3

| | Examples | | | | | | | | | Comp. Example |
|---|---|---|---|---|---|---|---|---|---|---|
| | 26 | 27 | 28 | 29 | 30 | 31 | 32 | 33 | 34 | 9 |
| sodium 2-naphthalenesulfonate | 3.0 | 3.0 | — | — | — | — | — | — | — | — |
| disodium 1-amino-8-naphthol-3,6-disulfonate | — | — | 3.0 | — | — | — | — | — | — | — |
| polycondensation product of sodium 2-naphthalenesulfonate and formalin* | — | — | — | 3.0 | — | — | — | — | — | — |
| sodium guaiazulenesulfonate | — | — | — | — | 3.0 | — | — | — | — | — |
| sodium 5,6,7,8-tetrahydro-2-naphthalenesulfonate | — | — | — | — | — | 3.0 | — | — | — | — |
| sodium 5-indansulfonate | — | — | — | — | — | — | 3.0 | — | — | — |
| sodium hydroxymethoxy-benzophenonesulfonate | — | — | — | — | — | — | — | 3.0 | — | — |
| disodium dihydroxydimethoxy-benzophenonedisulfonate | — | — | — | — | — | — | — | — | 3.0 | — |
| benzyl alcohol | — | 5.0 | — | 5.0 | 5.0 | — | 5.0 | — | 5.0 | 5.0 |
| 2-benzyloxyethanol | — | — | — | — | — | 5.0 | — | 5.0 | — | — |
| ethanol | — | 20.0 | — | 20.0 | 20.0 | 20.0 | 20.0 | 20.0 | 20.0 | 20.0 |
| water | balance | balance | balance | balance | balance | balance | balance | balance | balance | balance |
| tension/firmness immediately after treatment | A | A | A | A | A | A | A | A | A | D |
| tension/firmness after 4 shampoos | A | A | A | A | A | A | A | A | A | C |

(% by weight)

*weight-average degree of polycondensation: 8.2

While the invention has been described in detail and with reference to specific embodiments thereof, it will be apparent to one skilled in the art that various changes and modifications can be made therein without departing from the spirit and scope thereof.

What is claimed is:

1. A method for imparting elasticity to the hair which comprises first treating the hair with a first agent containing a reducing agent in an amount of 0.1 to 10% by weight based on the weight of the first agent and subsequently treating the hair with a second agent containing a sodium or potassium salt of naphthalenesulfonic acid, at least one organic solvent selected from the group consisting of benzyl alcohol, 2-benzyloxyethanol, N-methylpyrrolidone and an alkylene carbonate and at least one organic acid selected from the group consisting of lactic acid, glycolic acid, citric acid and malic acid.

2. The method of claim 1, wherein the content of the sodium or potassium salt of naphthalenesulfonic acid is 0.1 to 10% by weight based on the second agent.

3. The method of claim 1, wherein the content of the sodium or potassium salt of naphthalenesulfonic acid is from 1 to 5% by weight based on the second agent.

4. The method of claim 1, wherein the content of the at least one organic solvent is 0.5 to 50% by weight based on the second agent.

5. The method of claim 1, wherein the content of the at least one organic solvent is 2 to 30% by weight based on the second agent.

6. The method of claim 1, wherein the at least one organic acid is selected from the group consisting of lactic, glycolic and malic acid.

7. The method of claim 1, wherein the balance of the first and second agent comprises water.

8. The method of claim 7, wherein there is present at least one organic solvent and the ratio of the at least one organic solvent to water ranges from 20/80 to 50/50.

9. The method of claim 1, wherein the content of the reducing agent ranges from 1 to 7% by weight based on the weight of the first agent.

10. The method of claim 1, wherein there is further present in the first agent an alkaline substance to promote the reducing action of the reducing agent.

11. The method of claim 1, wherein a pH of the second agent is such as to sufficiently swell the hair and promote the penetration of the naphthalenesulfonic acid into the hair and wherein the reducing agent cleaves cysteine in the hair to make the hair swell to promote the penetration of the naphthalenesulfonic acid into the hair.

12. The method of claim 1, wherein the reducing agent is at least one compound selected from thioglycolic acid, cysteine, N-acetyl-L-cysteine and salts thereof, glycerolmonothioglycolate or thioglyceryl ether.

13. The method of claim 1, wherein said first agent consists essentially of the reducing agent and said second consists essentially of the sodium or potassium salt of naphthalenesulfonic acid, the at least one organic solvent and the at least one organic acid.

14. The method as claimed in claim 1, wherein said salt is the sodium salt of naphthalenesulfonic acid.

15. The method of claim 1, wherein the reducing agent is at least one compound selected from the group consisting of thioglycolic acid, cysteine, N-acetyl-L-cysteine, and salts thereof, glycerylmonothioglycolate, thioglyceryl ether, sulfites and hydrogen sulfites.

16. The method of claim 1, wherein said naphthalenesulfonic acid is represented by Formula (3):

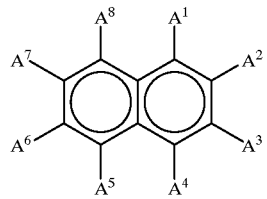

(3)

wherein at least one of $A^1$ to $A^8$ represents a sulfo group while others each represents a hydrogen atom, a halogen atom, a hydroxyl group, a nitro group, a carboxyl group, a lower alkoxycarbonyl group, an alkyl group, an alkenyl group, a lower alkoxy group, a formyl group, an acyl group, a phenylazo group which may be substituted or an —N(R')(R") group, wherein R' and R" each represents a hydrogen atom, a lower alkyl group, a lower alkenyl group, a phenyl group, a benzyl group or an acyl group.

17. A method for imparting elasticity to the hair which comprises first treating the hair with a first agent containing a reducing agent in an amount of 0.1 to 10% by weight based on the weight of the first agent and subsequently treating the hair with a second agent containing a sodium or potassium salt of naphthalenesulfonic acid, at least one organic solvent selected from the group consisting of benzyl alcohol, 2-benzyloxyethanol, N-methylpyrrolidone and an alkylene carbonate and at least one organic acid selected from the group consisting of lactic acid, glycolic acid, citric acid and malic acid, said second agent having a pH of from 2 to 5.

18. The method of claim 17, wherein the at least one organic acid is selected from the group consisting of lactic, glycolic and malic acid.

19. The method of claim 17, wherein the content of the sodium or potassium salt of naphthalenesulfonic acid is 0.1 to 10% by weight based on the second agent.

20. The method of claim 17, wherein the content of the sodium or potassium salt of naphthalenesulfonic acid is from 1 to 5% by weight based on the second agent.

21. The method of claim 17, wherein the content of the at least one organic solvent is 0.5 to 50% by weight based on the second agent.

22. The method of claim 17, wherein the content of the at least one organic solvent is 2 to 30% by weight based on the second agent.

23. The method of claim 17, wherein the balance of the first and second agents comprises water.

24. The method of claim 23, wherein the ratio of the at least one organic solvent to water ranges from 20/80 to 50/50.

25. The method of claim 17, wherein the content of the reducing agent ranges from 1 to 7% by weight based on the weight of the first agent.

26. The method of claim 17, wherein there is further present in the first agent an alkaline substance to promote the reducing action of the reducing agent.

27. The method of claim 17, wherein the pH of the second agent is such as to sufficiently swell the hair and promote the penetration of the naphthalenesulfonic acid into the hair and wherein the reducing agent cleaves cysteine in the hair to make the hair swell to promote the penetration of the naphthalenesulfonic acid into the hair.

28. The method of claim 17, wherein the reducing agent is at least one compound selected from thioglycolic acid, cysteine, N-acetyl-L-cysteine and salts thereof, glycerolmonothioglycolate or thioglyceryl ether.

29. The method as claimed in claim 17, wherein said salt is the sodium salt of naphthalenesulfonic acid.

30. The method of claim 17, wherein the reducing agent is at least one compound selected from the group consisting of thioglycolic acid, cysteine, N-acetyl-L-cysteine, and salts thereof, glycerylmonothioglycolate, thioglyceryl ether, sulfites and hydrogen sulfites.

31. The method of claim 17, wherein said naphthalenesulfonic acid is represented by Formula (3):

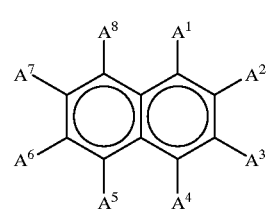

(3)

wherein at least one of $A^1$ to $A^8$ represents a sulfo group while others each represents a hydrogen atom, a halogen atom, a hydroxyl group, a nitro group, a carboxyl group, a lower alkoxycarbonyl group, an alkyl group, an alkenyl group, a lower alkoxy group, a formyl group, an acyl group, a phenylazo group which may be substituted or an —N(R')(R") group, wherein R' and R" each represents a hydrogen atom, a lower alkyl group, a lower alkenyl group, a phenyl group, a benzyl group or an acyl group.

* * * * *